(12) United States Patent
McIlrath

(10) Patent No.: US 9,499,450 B2
(45) Date of Patent: Nov. 22, 2016

(54) ELECTROSTATIC ADHESION OF DRY POWDERS TO MACRO FERTILIZERS

(71) Applicant: Compass Minerals Manitoba, Inc., Winnipeg, Manitoba (CA)

(72) Inventor: Michael McIlrath, Winnipeg (CA)

(73) Assignee: Compass Minerals Manitoba, Inc., Winnipeg, Manitoba (CA)

( * ) Notice: Subject to any disclaimer, the term of this patent is extended or adjusted under 35 U.S.C. 154(b) by 0 days.

(21) Appl. No.: 14/643,738

(22) Filed: Mar. 10, 2015

(65) Prior Publication Data

US 2016/0264486 A1 Sep. 15, 2016

(51) Int. Cl.
*C05G 3/00* (2006.01)
*C05C 9/00* (2006.01)
*A01C 1/06* (2006.01)
*A01N 25/08* (2006.01)

(52) U.S. Cl.
CPC .............. *C05G 3/0041* (2013.01); *A01C 1/06* (2013.01); *A01N 25/08* (2013.01); *C05C 9/005* (2013.01)

(58) Field of Classification Search
None
See application file for complete search history.

(56) References Cited

U.S. PATENT DOCUMENTS

| 3,475,154 | A | 10/1969 | Kato |
| 4,520,754 | A | 6/1985 | Gange et al. |
| 5,560,768 | A | 10/1996 | Gordonov et al. |
| 7,445,657 | B2 * | 11/2008 | Green .................... A01C 1/06 71/31 |

OTHER PUBLICATIONS

Compass Minerals Manitoba, Inc., PCT/CA2016/050262 filed Mar. 10, 2016, "The International Search Report and the Written Opinion of the Internation Searching Authority, or the Declaration", mailed Jul. 6, 2016.

* cited by examiner

*Primary Examiner* — Wayne Langel
(74) *Attorney, Agent, or Firm* — McKee, Voorhees & Sease, PLC

(57) ABSTRACT

A method for electrostatically adhering an agricultural input powder to an agronomic carrier is described. A dry nutrient powder is electrostatically charged in a charging chamber which has a grounded metal component such that the electrostatically charged powder moves towards the metal component. The agronomic carrier is then passed by the charged powder such that the charged powder adheres to the carrier.

**17 Claims,

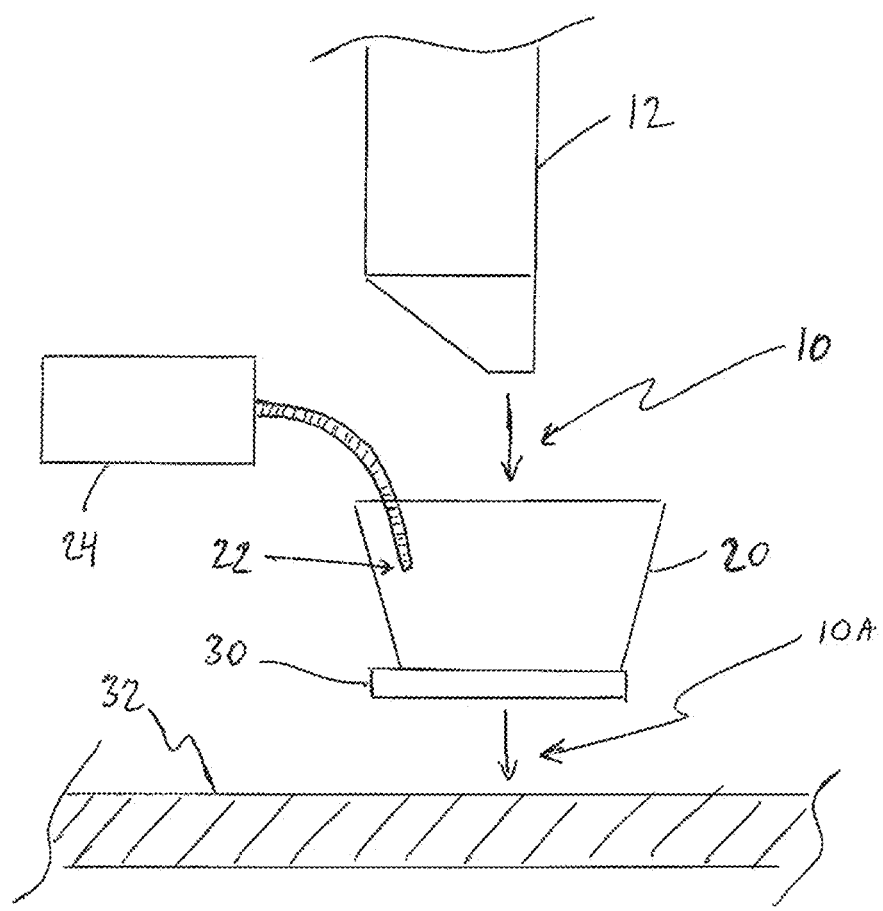

ELECTROSTATIC ADHESION OF DRY POWDERS TO MACRO FERTILIZERS

FIELD OF THE INVENTION

The present invention relates generally to the field of agricultural inputs. More specifically, the present invention relates to a method of coating an agronomic carrier with an agricultural input powder.

BACKGROUND OF THE INVENTION

Studies of powdered fertilizers or nutrients have shown them to be effective fertilizers, being essentially equivalent to granular applications. However, the practical considerations of applying powdered products on a field scale meant that these products have not been available to farmers and producers. For example, most oxide products come in high analysis (60-80 percent actual metal) while most micronutrients are applied in low units per land measure (e.g. 1-10 pounds actual per acre). Furthermore, many micronutrient products are applied in heterogeneous blends with other fertilizers (nitrogen phosphate etc.) These products and/or blends typically have densities in the 45-65 lb per cubic foot range. Existing micronutrient products are typically in the 95+ density range meaning that the blend does not hold its integrity during extended storage as is common in agriculture or if the product is transported over rough terrain. In addition, the higher density means that the nutrients are not spread evenly on the field.

Past work with powdered nutrients by the inventors has shown that it is possible to coat macro fertilizer with 0.1 to 2 percent weight to weight of powdered nutrients directly onto dry macro fertilizers such as urea, phosphate granules, potash granules and the like, without the use of binders, as discussed in U.S. Pat. No. 7,445,657. However, in some cases it can be difficult to obtain a coating above 1 percent (w/w) on certain carriers, for example, if the prills or granules have a substantially smooth surface or are larger than average. Furthermore, as discussed below, using this method, it is often only possible to coat the outer surface of the carrier with a single layer of the powder.

SUMMARY OF THE INVENTION

According to a first aspect of the invention, there is provided a method for adhering a nutrient powder to an agronomic carrier comprising:

electrostatically charging a quantity of dry powder of an agricultural input in a charging chamber comprising a grounded metal component such that the electrostatically charged powder coats the agronomic carrier which then moves towards the grounded metal component; and As will be apparent to one of skill in the art, an agricultural input refers generally to different types of factors which relate to agricultural productivity. These can include materials: that provide plant nutrition, for example, fertilizers; that provide crop protection, for example, pesticides and herbicides; that add specific biological activities to the soil, for example, inoculants; or materials that provide soil amending properties, for example, changing pH.

Examples of suitable agronomic carriers include but are by no means limited to granules, prills, seeds, fertilizer pellets, fertilizer prills, fertilizer granules, liming materials, gypsum, pelleted manures, inert carriers such as zeolite, organic grits or organic pellets.

Preferably, the electrostatic charge is applied to the powder at rates ranging from 15 kV to 100 kV. In other embodiments, the electrostatic charge may be applied at a rate ranging from between 25 kV to 100 kV, from 15 kV to 25 kV, from 15 kV to 50 kV, from 15 kV to 75 kV, from 25 kV to 75 kV, from 25 to 50 kV, from 50 to 75 kV, from 50 kV to 100 kV or from 75 kV to 100 kV.

Preferably, the electrostatic charging is carried out at an air pressure between 8 to 20 psi or 0-4 BAR.

Preferably, the particle size of the powders is of a size wherein at least 80 percent are between 10 and 90 microns.

According to another aspect of the invention, there is provided a fertilizer product comprising a dry agronomic carrier coated with a fine dry powder of at least one agricultural input, wherein the agricultural input powder has been ground such that at least half of the particles are of an average diameter between 10 and 90 microns, said powder being present on the carrier at 0.1%-5.0% (w/w) of the carrier.

BRIEF DESCRIPTION OF THE DRAWINGS

FIG. 1 is a schematic diagram of the method of the invention.

DETAILED DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Definitions

As used herein, "nutrient" refers to micronutrients, secondary nutrients and macronutrients, as well as soil amendments, for example, zinc, copper, manganese, boron, calcium, iron, calcium sulfate (gypsum), magnesium, molybdenum, chloride, selenium, phosphate, nitrogen, potassium and sulfur.

As used herein, "micronutrients" refers to elements required in small or trace amounts for plant growth, for example, molybdenum, nickel, copper, zinc, manganese, boron, iron and chloride.

As used herein, "macronutrients" refers to elements typically required in large amounts for plant growth, for example, phosphorus, magnesium, calcium, potassium, nitrogen, oxygen, carbon and hydrogen.

As used herein, "higher analysis" refers to guaranteed minimum analysis. That is, higher analysis means higher concentration of active ingredients versus carriers or impurities.

As used herein, "density" refers to kilograms per cubic meter.

As used herein, "agronomic carrier" refers to an agricultural product, for example, but by no means limited to: seeds; nitrogen, phosphate, potassium, sulfur, calcium and/or magnesium fertilizer products; urea prills; dry or granular fertilizer products; and inert or biodegradable pellets.

As used herein, "electrostatic charge" refers to an electrical discharge or contact electrification in which ions are generated and/or transferred.

The electrostatic charge can be applied by any suitable means known in the art. One example is triboelectric charging, which is a type of contact electrification in which certain materials become electrically charged after they come into contact with another different material. Another example is corona discharge wherein ions are generated and passed to nearby areas of lower potential.

As discussed herein, the inventors have conducted tests in order to address the difficulties discussed above. Specifically, the inventors have determined that the maximum coating capacity can be increased by subjecting the powder to a fertilizer handling system which comprises applying an electrostatic charge to the powder.

According to an aspect of the invention, there is provided a method for adhering an agricultural input powder to an agronomic carrier comprising:

electrostatically charging a quantity of dry agricultural input powder in a charging chamber comprising a grounded metal component and bringing the agronomic carriers in contact with the ground such that the carrier becomes grounded such that the electrostatically charged powder moves towards the grounded agronomic carrier; and passing the agronomic carriers by the charged powder such that the charged powder adheres to the carrier.

It is of note that "passing" refers to the agronomic carriers being moved past the reservoir of charged agricultural input powder in sufficient proximity to the powder that the powder will adhere to the carrier, as discussed below.

As will be appreciated by one of skill in the art, the invention can also be considered a method for coating an agronomic carrier with an agricultural input powder.

Preferably, the electrostatic charge is applied to the powder at rates ranging from 15 kV to 100 kV. In other embodiments, the electrostatic charge may be applied at a rate ranging from between 25 kV to 100 kV, from 15 kV to 25 kV, from 15 kV to 50 kV, from 15 kV to 75 kV, from 25 kV to 75 kV, from 25 to 50 kV, from 50 to 75 kV, from 50 kV to 100 kV or from 75 kV to 100 kV.

Preferably, the electrostatic charging was carried out an air pressure between 0 TO 4 BAR.

As will be apparent to one of skill in the art, an "agricultural input" refers generally to different types of factors which relate to agricultural productivity, in the context of the instant invention, these can include for example but by no means limited to materials that provide plant nutrition, for example, fertilizers; that provide crop protection, for example, pesticides and herbicides; that add specific biological activities to the soil, for example, inoculants; or materials that provide soil amending properties. As is known to one of skill in the art, a soil amendment is any material added to a soil to improve its physical properties, such as water retention, permeability, water infiltration, drainage, aeration and structure. The goal of soil amendment is to provide a better environment for roots.

Examples of suitable agronomic carriers include but are by no means limited to granules, prills, seeds, fertilizer pellets, fertilizer prills, fertilizer granules, liming materials, gypsum, pelleted manures, inert carriers such as zeolite, organic grits or organic pellets. The agricultural input powder may be, for example, a powdered fungicide, an insecticide, a nutrient such as nitrogen, phosphorus, potassium, calcium, magnesium; a fertilizer powder or component thereof; an inoculant, a soil amendment, or a micronutrients such as zinc, copper, manganese, boron, iron, magnesium, molybdenum, chloride, selenium, phosphate, nitrogen, potassium, sulfur or combinations thereof. By way of illustrative but in no way limiting examples, copper may be copper (cupric): hydroxide, chloride, sulfate, oxide, oxysulfate, nitrate, carbonate, ammonium carbonate, cupric chloride dihydrate, proteinate, acetate, citrate, chelate, complex, or sequestered; zinc may be zinc: acetate, amoniated zinc, ammonium chloride, sulfate, oxide, oxysulfate, nitrate, chloride, citrate, chelate, or complex sequestered; manganese (manganous) may be manganese: nitrate, chloride, sulfate, oxide, oxysulfate, acetate anhydrous, carbonate, potassium manganese sulfate, acetate tetrahydrate, nitrate hexahydrate, citrate, chelate, or complex sequestered. Boron may be: boric acid, sodium borate, potassium tetraborate tetrhydrate, calcium borate, calcium-sodium borate, (disodium octoborate tetrahydrate), (orthoboric acid), or Calcium may be calcium: carbonate, chloride, sulfate, gypsum, calcium borate, lime, nitrate, phosphate, citrate, chelate, or complex sequestered; and Iron may be iron: sulfate, sulfate anhydrous, chloride, tetrahydrate, hexahydrate, nitrate, nitrate nonahydrate, chloride hexahydrate, ammonium citrate, ammonium sulfate, chelate, sequestered, proteinate or complex.

In some embodiments, the powder may be comprised of at least one nutrient in an oxide form, in a sulfate form or a combination of oxide and sulfate forms, as discussed below The oxide form of the nutrient or nutrient powder may be, for example, copper oxide, produced, for example, by pyrolysis of copper nitrate, zinc oxide, produced, for example, by pyrolysis of zinc nitrate or carbonate, manganese oxide or the like or boric acid, manganese sulfate or the like. As will be appreciated by one knowledgeable in the art, other nutrients or nutrient powders may be similarly prepared using means known in the art.

As will be apparent to one knowledgeable in the art, the nutrient or nutrient powder may have any suitable or desirable nutrient concentration, whether a single nutrient or a combination thereof. That is, the concentration of the nutrient(s) may vary from 1-99%, depending upon intended use and application conditions. In some embodiments, the fertilizer may have a nutrient concentration of, for example: 5-45% zinc; 5-45% copper; 5-45% manganese or a mixture of 7% copper, 7% zinc and 6% magnesium. As will be apparent to one knowledgeable in the art, the concentrations of the nutrients may be varied according to customer preference, soil conditions and/or need, depending on the circumstances.

As will be apparent to one of skill in the art, the individual nutrients may be at any suitable level, for example, from trace amounts or 0.1% to 50% actual.

The agricultural input powder is a dry, fine powder, typically ground or otherwise prepared or manipulated such that at least half of the particles are of an average diameter between 10 and 90 microns in size.

As discussed herein, the inventors have been found that the instant method can be used to apply a powder coating to an agronomic carrier of between 0.1% (w/w) to 5% (w/w) or of between 0.1% (w/w) to 4% (w/w) of the weight of the agricultural carrier. In other embodiments, the coating is between 1.0% (w/w) to 5% (w/w) or 1.0% (w/w) to 4% (w/w). In yet other embodiments, the agricultural input powder is between 1.5% (w/w) to 5% (w/w) or between 1.5% (w/w) to 4.0% (w/w). In yet other embodiments, the agricultural input powder is between 2.0% (w/w) to 5% (w/w) or between 2.0% (w/w) to 4.0% (w/w). In still other embodiments, the agricultural input powder is between 2.5% (w/w) to 5% (w/w) or between 2.5% (w/w) to 4.0% (w/w). As discussed in U.S. Pat. No. 7,445,657, the inventors previously hypothesized that static electricity generated during the mixing process promoted adhesion of the powder to the carrier but that this was not an essential feature of the invention.

As will be appreciated by one of skill in the art, static electric charges are very difficult to measure accurately. In addition, static electric charges can be difficult to reproduce consistently as several factors influence the generation of static electricity.

Furthermore, while the process disclosed in U.S. Pat. No. 7,445,657 is very effective at coating an agronomic carrier, under certain conditions and/or certain combinations of nutrient powders and agronomic carriers, the nutrient powder may not be spread evenly on the carrier or be spread at the desired density. Furthermore, the process can also generate a moderate amount of dust during the application process which results in some loss of powder and also requires workers to take precautions to prevent inhaling the dust.

As will be apparent to one of skill in the art, this method is highly effective at providing a single layer of powder on a carrier, but is not suitable for over-coating a carrier or for applying one or more "coats" of different agricultural input powder to a carrier.

That is, the carrier will be coated with more than a single layer of the agricultural input. In some embodiments, the carrier may be coated with a single agricultural input powder between 0.1% (w/w) to 5% (w/w) as discussed above or the agricultural carrier may be coated with two or more agricultural input powders, wherein each powder forms a separate layer or coating around the carrier.

Accordingly, in another aspect of the invention, there is provided a fertilizer product comprising a dry agronomic carrier coated with a fine dry powder of at least one agricultural input, wherein the agricultural input powder has been ground such that at least half of the particles are of an average diameter between 10 and 90 microns, said powder being present on the carrier at 0.1%-5.0% (w/w) of the carrier.

In an attempt to increase application rates, the inventors tested adding minute amounts of liquid in an effort to encourage powder to powder binding and thereby increasing coating of the agronomic carrier. As discussed in U.S. Pat. No. 7,445,657, the addition of liquids such as binders can damage some carriers, causing either a breakdown in the integrity of the carrier or in the case of seeds, reducing emergence efficiency. Furthermore, the addition of the liquid only increased binding by approximately 50% over the single layer surface area coating attained with direct dry to dry application.

Subsequently however, as discussed herein, it has been discovered that applying an electrostatic charge of between 15 kV to 100 kV, preferably, in some embodiments, 75 kV to 100 kV, under an air pressure of 8 to 20 psi promotes greater adhesion of the powder to the carrier, as discussed below.

As a result of carrying out the process under air pressure, the powder flows in a directable jet, which improves coating of the carrier, as discussed herein. Specifically, the pressure helps to better distribute the agricultural input powder during the coating process.

Furthermore, the combination of the generated electrostatic charge and the air pressure promotes increased adhesion to the carrier, specifically, the air pressure directs the powder towards the carrier but also disperses the particles so that individual particles of the powder are charged, thereby improving adhesion of the powder.

As will be readily apparent to one of skill in the art, as a result, much higher coatings, for example, 4-5% can be attained using this method.

Furthermore, in some embodiments, the combination of the electrostatic charge and the air pressure reduces dust, as discussed below.

As will be appreciated by one of skill in the art, by virtue of the coating rates now attainable, multiple layers of powder may be applied so that different agricultural inputs may be applied to a single carrier, for example, a pesticide and a fertilizer or a fungicide and an inoculant. Other suitable combinations will be readily apparent to one of skill in the art and are within the scope of the invention.

Referring to FIG. 1, the method of the invention is shown schematically in one possible embodiment or arrangement. Therein, the agricultural input, indicated as a nutrient powder, is released from a feeder into a charging chamber which includes electrodes powered by an electrical generator. As discussed above, the agricultural input powder is electrostatically charged within the charging chamber. The charged agricultural input powder is then released from the charging chamber such that the charged powder comes into contact with the agronomic carrier, indicated in FIG. 1 as being granular fertilizer products, thereby coating the agronomic carrier. As will be apparent to one of skill in the art, other suitable arrangements for applying a charged agricultural input powder to an agronomic carrier are also within the scope of the invention and this arrangement is intended for illustrative purposes only.

In preferred embodiments, there is provided a method for electrostatically adhering fine, dry nutrient particles in powder form to agronomic carriers such as granular fertilizers or planting seed, which comprises the steps of:

Feeding nutrient particles (powder) into a charging chamber or through a charging point along the blending pathway.

In the charging chamber introducing (a) a charge such that a metal component (stinger, paddle, auger or other surface) is grounded, and (b) the desired powder through an electrostatic charging system (such as a triboelectric gun or corona discharge apparatus) wherein the powder will preferentially take two steps (i) it will drive towards the grounded surface and then (ii) it will then move onto the granular carrier as the carrier particles pass by or contact the metal surface that is coated with the powder.

This results in an amount of powder adhesion that is much higher than can be achieved with mechanical agitation. Furthermore, there is a reduction in the amount of dust because of the preferential movement of the powder particles to the charged surface One embodiment of the system for carrying out the method or process of the invention is shown schematically in FIG. 1.

As will be appreciated by one of skill in the art, other suitable arrangements are within the scope of the invention and this embodiment is provided for illustrative purposes.

Therein, an agricultural input powder 10 is released from feeder 12 into charging chamber 20. The charging chamber 20 includes grounded metal component 22 which is connected to an electrical generator 24. As discussed above, while the agricultural input powder 10 is within the charging chamber, the particles of the powder are charged. The charged agricultural input powder 10A particles are then released from the charging chamber 20. In some embodiments, the release of the charged agricultural input powder 10A particles is regulated and/or facilitated by a spreader 30 at a base of the charging chamber 20 which promotes separation of the particles. Specifically, the charged agricultural input powder 10A particles are released from the charging chamber 20 onto a belt conveying agronomic carriers 32 to be coated. As discussed above, the charged agricultural input powder 10A particles adhere to and coat the agronomic carriers 32.

The invention will now be explained by way of examples; however, the invention is not necessarily limited by the examples.

A metallic container was used in a lab scale experiment to mimic a full scale fertilizer blending container. A metallic beater was used to represent a moving blender part (such as a paddle, baffle, stinger or auger).

The container and metallic beater were grounded (negatively charged). Then the metallic container was filled with 500 to 1000 gram samples of urea. The granules were put into motion.

Powdered (a) iron and (b) boron were delivered into the container via a charging gun (corona). The gun was charged at rates ranging from 75 to 100 kV and air pressure was delivered at 8 to 20 psi. Total amount adhering onto the urea or sulphur was weighed. The powder was 100 to 325 mesh in the trial.

The whole process was repeated, this time using only mechanical mixing to attain coatings of the powders onto the urea or sulphur.

Results

1) Iron Powder Coating on to Urea Prills

| Treatment | Descriptor | % coated (w/w) | Dust evaluation |
|---|---|---|---|
| Standard coating (direct application without electrical charge) | Add powdered nutrient blend and mix mechanically | 0.63 | Moderate dust in work area |
| Electrocharge gun/air pressure (charge applied to particles, blender surface grounded, urea positively charged by induction from the ground) | Add nutrient powder to urea through electrically charged "gun" with air pressure | 1.5 | Little dust in work area |

Note that (a) the total amount adhering to the urea particles was more than doubled when a charged system under light air pressures were introduced, and (b) there was a noticeable reduction in dust in the work area 2) Boron Powder Coating on to Urea Prills

| Treatment | Descriptor | % coated (w/w) | Dust evaluation |
|---|---|---|---|
| Standard coating (direct application without electrical charge) | Add powdered nutrient blend and mix mechanically | 0.82 | Moderate dust in work area |
| Electrocharge gun/air pressure (charge applied to particles, blender surface grounded, urea positively charged by induction from the ground) | Add nutrient powder to urea through electrically charged "gun" with air pressure | 1.48 | Little dust in work area |

Note that (a) the total amount adhering to the urea particles was more than doubled when a charged system under light air pressures were introduced, and (b) there was a noticeable reduction in dust in the work area.

While the preferred embodiments of the invention have been described above, it will be recognized and understood that various modifications may be made therein, and the appended claims are intended to cover all such modifications which may fall within the spirit and scope of the invention.

What is claimed is:

1. A method for adhering an agricultural input powder to an agronomic carrier comprising:

providing an agricultural input powder wherein at least half of the particles of the powder are of an average diameter between about 10 and about 90 microns in size;

providing an electrostatic charging chamber comprising electrodes for charging particles of powder;

providing a grounded metal component and agronomic carriers to be coated;

applying air pressure to the powder such that the powder flows as a directable jet through the charging chamber where the particles of the powder are electrostatically charged by the electrodes, said electrostatically charged powder being driven towards the grounded metal component; and bringing the agronomic carriers in contact with the grounded metal component such that the electrostatically charged powder moves onto and adheres to the carrier.

2. The method according to claim 1 wherein the electrostatic charge is applied to the agronomic input powder at from 15 to 100 kV.

3. The method according to claim 1 wherein the charging chamber is at an air pressure between 0-4 BAR.

4. The method according to claim 1 wherein the agronomic carrier is selected from the group consisting of: seeds; nitrogen fertilizer products; phosphate fertilizer products; potassium fertilizer products; sulfur fertilizer products; calcium fertilizer products; magnesium fertilizer products; urea prills; dry fertilizer products; granular fertilizer products; inert pellets; and biodegradable pellets.

5. The method according to claim 1 wherein the agricultural input powder is selected from the group consisting of: a fungicide; an insecticide; a nutrient; a fertilizer powder or component thereof; an inoculant; a soil amendment; a micronutrient; and combinations thereof.

6. The method according to claim 1 wherein at least 50% of the powder passes through a 100 MESH screen.

7. The method according to claim 1 wherein the powder is between 100 MESH to 450 MESH.

8. The method according to claim 1 wherein the powder is between 100 MESH to 325 MESH.

9. The method according to claim 5 wherein the agricultural input is a nutrient and the nutrient is selected from the group consisting of: nitrogen, phosphorus, potassium, calcium and magnesium.

10. The method according to claim 5 wherein the agricultural input is selected from the group consisting of zinc, copper, manganese, boron, iron, calcium, magnesium, molybdenum, chloride-based compounds, selenium, phosphorus, nitrogen, potassium, and sulfur.

11. The method according to claim 1 where the electrostatic charge is applied at a rate between 25 kV to 100 kV.

12. The method according to claim 1 where the electrostatic charge is applied at a rate between from 15 kV to 25 kV.

13. The method according to claim 1 where the electrostatic charge is applied at a rate between from 15 kV to 50 kV.

14. The method according to claim 1 where the electrostatic charge is applied at a rate between from 15 kV to 75 kV.

15. The method according to claim 1 where the electrostatic charge is applied at a rate between from 25 kV to 75 kV.

16. The method according to claim 1 where the electrostatic charge is applied at a rate between from 25 to 50 kV.

17. The method according to claim 1 wherein the air pressure disperses the powder into individual particles, thereby improving adhesion of the charged powder to the agronomic carrier.

* * * * *